United States Patent [19]

Hesse et al.

[11] Patent Number: 5,472,957
[45] Date of Patent: Dec. 5, 1995

[54] CHEMICAL COMPOUNDS AND PROCESS

[75] Inventors: Robert H. Hesse, Cambridge, Mass.; Ezio Rizzardo, Wheelers Hill, Australia; Derek H. R. Barton, College Station, Tex.

[73] Assignee: Research Institute for Medicine and Chemistry, Cambridge, Mass.

[21] Appl. No.: 104,496

[22] Filed: Aug. 10, 1993

Related U.S. Application Data

[63] Continuation of Ser. No. 959,565, Oct. 13, 1992, abandoned, which is a continuation of Ser. No. 437,107, Nov. 16, 1989, abandoned, which is a continuation of Ser. No. 834,761, Feb. 28, 1986, abandoned, which is a continuation of Ser. No. 603,833, Apr. 25, 1984, abandoned, which is a continuation of Ser. No. 436,298, Oct. 25, 1982, abandoned, which is a continuation of Ser. No. 265,966, May 21, 1981, abandoned, which is a continuation of Ser. No. 131,036, Mar. 17, 1980, abandoned, which is a division of Ser. No. 30,636, Apr. 16, 1979, abandoned, which is a continuation of Ser. No. 805,911, Jun. 13, 1977, abandoned, which is a continuation of Ser. No. 538,258, Jan. 3, 1975, abandoned, which is a continuation-in-part of Ser. No. 362,339, May 21, 1973, Pat. No. 3,901,928, which is a continuation-in-part of Ser. No. 322,462, Jan. 10, 1973, abandoned.

[30] Foreign Application Priority Data

Jan. 9, 1974 [AU] Australia ............................. 64349/74

[51] Int. Cl.$^6$ ................................................. A61K 31/59
[52] U.S. Cl. ............................................................ 514/167
[58] Field of Search ............................................ 514/167

[56] References Cited

U.S. PATENT DOCUMENTS

| 2,840,575 | 6/1958 | Koevoet et al. | 260/397.2 |
| 2,862,934 | 12/1958 | Koevoet et al. | 260/397.2 |
| 3,741,996 | 6/1973 | Deluca et al. | 260/397.2 |
| 4,310,522 | 1/1982 | Frank | 424/236 |

Primary Examiner—Zohreh Fay
Attorney, Agent, or Firm—Bacon & Thomas

[57] ABSTRACT

The invention provides novel compositions for use in pharmaceutical and veterinary medicine which contain 1α-hydroxy vitamin D compounds. Particular compositions are described which contain steroids which induce or assist in combatting osteoporosis together with 1α-hydroxy vitamin $D_3$ or 1α,25-dihydroxy vitamin $D_3$. Methods of treatment of diseases are also provided including many which are resistant to vitamin $D_3$, in particular bone diseases.

13 Claims, No Drawings

CHEMICAL COMPOUNDS AND PROCESS

This application is a continuation of Ser. No. 07/959,565 filed Oct. 13, 1992; now abandoned which is a is a continuation of Ser. No. 07/437,107 filed Nov. 16, 1989, now abandoned; which is a continuation of Ser. No. 06/834,761 filed Feb. 28, 1986; now abandoned which is a continuation of Ser. No. 06/603,833 filed Apr. 25, 1984, now abandoned; which is a continuation of Ser. No. 06/436,298 filed Oct. 25, 1982, now abandoned; which is a continuation of Ser. No. 06/265,966 filed May 21, 1981, now abandoned; which is a continuation of Ser. No. 06/131,036 filed Mar. 17, 1980; now abandoned which is a division of Ser. No. 06/030,636 filed Apr. 16, 1979; now abandoned which is a continuation of Ser. No. 05/805,911 filed Jun. 13, 1977, now abandoned; which is a continuation of Ser. No. 05/538,258 filed Jan. 3, 1975, now abandoned; which is a continuation-in-part of Ser. No. 05/362,339 filed May 21, 1973, now U.S. Pat. No. 3,901,928; which is a continuation-in-part of Ser. No. 05/322,462, filed Jan. 10, 1973, now abandoned.

This invention relates to compositions containing $1\alpha$-hydroxy vitamin D derivatives and methods for their utilisation in human and veterinary medicine.

Our aforesaid application Ser. No. 362,339 describes as new compounds $1\alpha$-hydroxy-25-hydrogen-vitamin D derivatives, especially $1\alpha$-hydroxy vitamin $D_2$ and $1\alpha$-hydroxy vitamin $D_3$, including both $1\alpha$-hydroxy derivatives of the natural vitamins (which are in the cis form) but also the corresponding trans compounds. These new vitamins are superior in vitamin activity not only to vitamin $D_2$ and vitamin $D_3$, but also to the known $1\alpha,25$-dihydroxy vitamin $D_3$. Thus, for example, the $1\alpha$-hydroxy-25-hydrogen compounds exhibit a much more potent effect on bone metabolism; our tests in the vitamin $D_3$ series show that $1\alpha$-hydroxy-25-hydrogen vitamin $D_3$ is at least 10–50 times more active than unsubstituted vitamin $D_3$, while $1\alpha,25$-dihydroxy vitamin $D_3$ is reportedly only 2–5 times more active than the unsubstituted vitamin. These results are particularly surprising in view of previous suggestions that the 25-hydroxy group is involved in metabolism and should therefore be activity promoting. The new $1\alpha$-hydroxy-25-hydrogen vitamin D compounds are also-quick acting and their biological effect is rapidly terminated, so that the previously encountered problems of vitamin toxicity are substantially avoided by their use. It has not previously been published, incidentally, that $1\alpha,25$-dihydroxy vitamin $D_3$ was effective against diseases of bone metabolism such as osteoporosis.

$1\alpha$-Hydroxy-25-hydrogen vitamin D compounds, together with $1\alpha$-hydroxy-9,10-dihydrotachysterol, thus constitute an important new class of biologically active materials capable of, inter alia, stimulating intestinal calcium transport, bone calcium mobilisation, bone mineralisation and bone formation and pharmaceutical compositions containing effective amounts of one or more of these compounds and methods of treatment in human and veterinary medicine involving their administation comprise features of the present invention.

We have further found that if the final stages of synthesis of the $1\alpha$-hydroxy resin D compounds are not carefully controlled and the products efficiently separated, non-crystalline mixtures of isomers are obtained which are markedly unstable on storage, apart from being of lower activity than the pure $1\alpha$-hydroxy vitamin D. It is consequently preferred that the $1\alpha$-hydroxy vitamin D compounds used in the compositions and methods of the present invention should be crystalline and/or substantially free from isomeric material or other impurities arising from manufacture.

The said compounds have important prophylactic and therapeutic applications in the prevention or treatment of disorders such as rickets and osteomalacia and are of value in the treatment of both vitamin D responsive and vitamin D resistant diseases such as hypoparathyroidism, hypophosphataemia, phyocalcaemia and/or associated bone disease, renal disorders or renal failure and hypocalcaemic tetany. Furthermore, the superior activity of $1\alpha$-hydroxy-25-hydrogen vitamin D compounds and $1\alpha$-hydroxy-9,10-dihydrotachysterol in comparison with conventional 1-hydrogen vitamin D compounds renders the $1\alpha$-hydroxy compounds of value where vitamin D should be avoided because of its cumulative toxicity and, in particular, in the treatment of disorder such as vitamin D resistant rickets, renal osteodystrophy, steatorrhea, biliary cirrhosis and other malfunctions of absorption, osteoporosis, secondary hyprocalcaemia and/or bone disease arising from dysfunction of the liver, kidney or gastrointestinal tract, and secondary hypocalcaemia, osteoporosis or other bone diseases resulting from treatment with steroids, such as corticoids, diphenylhydantoin, barbituates such as phenylbarbitone, and related drugs, which prove refractory to conventional compounds such as vitamin $D_3$.

In general $1\alpha$-hydroxy-25-hydrogen vitamin D compounds and $1\alpha$-hydroxy-9,10-tachysterol may be administered parenterally in combination with an injectable liquid carrier such as sterile pyrogen-free water, sterile peroxide-free ethyl oleate, dehydrated alcohol, propylene glycol or a dehydrated alcohol/propylene glycol mixture. Such compositions may be injected intravenously, intraperitoneally or intramuscularly. Injectable compositions are preferably prepared in dosage unit for, e.g. in ampoules, each unit advantageously containing 0.02 to 200 µg, preferably 0.1–200 µg, advantageously containing 0.02 to 20 µg of the active vitamin ingredient in the case of the vitamin $D_2$ and $D_3$ compounds; the tachysterol compound requires doses in the upper part of the range. The normal dosage for adult human treatment will generally be in the range 0.02 to 200 µg, preferably 0.1–200 µg per day, lower dosages within this range, e.g. 0.02 to 5 µg, preferably 0.1–2 µg being used in prophylaxis and higher dosages, e.g. 5–50 µg being used in some therapeutic applications.

In view of the susceptibility of $1\alpha$-hydroxy vitamin D compounds and $1\alpha$-hydroxy-9,10-dihydrotachysterol to oxidation, we generally prefer that pharmaceutical compositions containing these materials should include at least a trace of an antioxidant such as ascorbic acid, butylated hydroxyanisole, butylated hydroxytoluene or hydroquinone.

We have also found, to our considerable surprise, that the $1\alpha$-hydroxy vitamin D compounds and $1\alpha$-hydroxy-9,10-dihydrotachsterol exhibit significant activity on oral administration, $1\alpha$-hydroxy-vitamin $D_3$ being outstanding in this respect. This is completely unexpected in view of previous disclosures relating to $1=,25$-dihydroxy vitamin $D_3$, which have indicated that chronic oral doses of the dihydroxy vitamin have very low activity (e.g. as determined by antirachitic activity or the elevation of serum calcium) and that parenteral administration of the dihydroxy vitamin is necessary to achieve beneficial therapeutic results; one would normally have expected $1\alpha$-hydroxy vitamin D compounds to show analogous general behaviour to the corresponding dihydroxy vitamin in view of the similarity in the nature of the biological activity of the compounds in other respects. In fact, our own experiments have shown that $1\alpha,25$-dihydroxy vitamin D, prepared in a form substantially free from isomeric or other impurities arising from its manufacture, preferably by crystallisation, does have oral activity of the same order as 1α-hydroxy vitamin D; this unexpected finding means that the dihydroxy vitamin can be used in oral formulations (whereas this was previously thought unsuitable) provided it is in a sufficiently pure and hence stable form.

The following table which shows the effect on serum calcium and phosphorus levels for parathyroidectomised/thyroidectomised rats (these being male Charles River rats weight 80–100 g, each test group comprising 6 rats) of oral administration of 1α-hydroxy vitamin $D_3$ (0.1 μg/kg via a gastric intubation), demonstrates that 1α-hydroxy vitamin $D_3$ exhibits good activity an oral administration, as evidenced by the rise in serum calcium level relative to the untreated controls. The table also indicates that the metabolic changes induced by 1α-hydroxy vitamin $D_3$ are of comparatively short duration, the serum calcium level in the 1α-hydroxy vitamin $D_3$—treated rats approaching closely that of the control rats within 24 hours from administration of the vitamin. This confirms that 1α-hydroxy vitamin $D_3$ is rapidly eliminated by the system and so is less likely to produce undesirable vitamin poisoning side effects.

TABLE 1

Effects of orally administered 1α-hydroxy vitamin $D_3$ on serum calcium ard phosporus levels in parathyroidectomised/thyroidectomised rats

| Vitamin administered | Serum calcium level (mg/100 ml) | | Serum phosphorus level (mg/100 ml) | |
|---|---|---|---|---|
| | 8 hrs after administration | 24 hrs after administration | 8 hrs after administration | 24 hrs after administration |
| — (control) | 4.5 ± .43. | 4.8 ± .46 | 12.0 ± .44 | 14.1 ± 1.9 |
| 1α-hydroxy vitaimin $D_3$ | 9.9 ± .80 | 6.4 ± .73 | 9.5 ± 1.1 | 14.5 ± 1.0 |

The oral activity and consequent ease of administration of 1α-hydroxy vitamin $D_3$ render this compound of very considerable therapeutic value over a wide range of applications, and considerably enhance the utility of the compound over the known 1α,25-hydroxy vitamin D derivatives. Additional advantages of 1α,25-hydrogen vitamin D derivatives are the increased stability with respect to 1α,25-dihydroxy vitamin D derivatives as well as the ease of preparation, purification and the lower cost of therapy.

The new 1α-hydroxy compounds may, for example, be used as food supplements or components of food supplements, e.g. in combination with other vitamins. One example of such an application is in the fortification of milk, incorporation of 0.1–0.5 μg of 1α-hydroxy vitamin $D_3$ per quart of milk being of value prophylactically in the prevention of disorders such as rickets, osteomalacia etc.

Similarly, the new 1α-hydroxy compounds may be presented in orally administrable pharmaceutical compositions for a wide range of applications, e.g. the treatment of any of the above-mentioned vitamin D responsive or, alternatively any of the 1α-hydroxy vitamin D responsive— conventional vitamin in D refractory diseases, particularly the long-term treatment of diseases such as osteoporosis, and prophylactic applications such as vitamin and multi-vitamin preparations.

Orally administrable compositions containing the new 1α-hydroxy compounds may, if desired, contain one or more physiologically compatible carriers and/or excipients and may be solid or liquid. The compositions may take any convenient form including, for example, tablets, coated tablets, capsules, lozenges, aqueous or oily suspensions, solutions, emulsions, syrups, elixirs and dry products suitable for reconstitution with water or another suitable liquid vehicle before use. The compositions are preferably prepared in dosage unit form, each unit advantageously containing 0.02 to 20 μg, preferably 0.2 μg, more preferably 0.5–5 μg of 1α-hydroxy compound. The dosage of 1α-hydroxy vitamin $D_3$ employed for adult human treatment will typically be in the range 0.02 to 5.0 μg per day. 1α-hydroxyvitamin $D_2$ is given at similar doses but 1α-hydroxy-9,10-dihydrotachysterol is given at higher doses, e.g. up to 200 μg/day. Tablets and capsules containing the new 1α-hydroxy compounds may, if desired, contain conventional ingredients such as binding agents, for example syrup, acacia, gelatin, sorbitol, tragacanth or polyvinyl-pyrolidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. Tablets may be coated according to methods well known in the art.

Liquid 1α-hydroxy vitamin $D_3$ compositions may contain conventional additives such as suspending agents, for example sorbitol syrup, methyl cellulose, glucose/sugar syrup, gelatin, hydroxymethycellulose, carboxymethylcellulose, aluminium stearate gel or hydrogenated edible fats, emulsifying agents, for example lecithin, sorbitan monooleate or acacia; non-aqueous vehicles, which may include edible oils, for example vegetable oils such as arachis oil, almond oil, fractionated coconut oil, oily esters such as polysorbate 80, propylene glycol, or ethyl alcohol; and preservatives, for example methyl or propyl p-hydroxybenzoates or sorbic acid. Liquid compositions may conveniently be encapsulated in, for example, gelatin to give a product in dosage unit form.

The compositions of the invention may contain other therapeutically useful ingredients such as calcium salts (e.g. the lactate, sodium lactate, phosphate, gluconate or hypophosphite) and/or salts of other essential trace elements such as magnesium, maganese, iron, copper, zinc and iodine and/or other vitamins such as vitamin A, vitamin $D_1$, vitamin $B_2$, nicotinamide, pantothenic acid or salts thereof e.g. the calcium salt, vitamin $B_6$, vitamin $B_{12}$ folic acid, vitamin C and vitamin E. Multi-vitamin preparations incorporating the new 1α-hydroxy compounds may be formulated in an analogous manner to such vitamin preparations employing conventional 1-hydrogen vitamin D compounds.

The activity of the new 1α-hydroxy compounds also renders the compound suitable for rectal administration, and pharmaceutical compositions for this purpose, e.g. containing an effective dose of 1α-hydroxy vitamin $D_3$ in admixture with a conventional suppository base such as cocoa butter or another glyceride fall within the scope of the invention.

As indicated above, it may be advantageous to incorporate an antioxidant, for example ascorbic acid, butylated hydroxyanisole or hydroquinone in the compositions of the invention to enhance their storage life.

The following particular disorders, which cannot be treated with vitamin D, may be successfully treated with 1α-hydroxy vitamin $D_3$:

Steroid induced osteoporosis

Treatment of this condition may be effected by daily administration of 0.02 to 5.0 μg, preferably 0.1 to 2.0 μg of 1α-hydroxy vitamin $D_3$.

Prophylaxis is particularly effective, that is the substantially simultaneous administration of a steroid which induces osteoporosis and 1α-hydroxy vitamin D$_3$. This is especially effective at the beginning of steroid therapy, to avoid actual bone lesions. The steroid may, for example, be an antiinflammatory corticosteroid, e.g. betamethasone, triamcinnolone, dexamethasone, prednisolone or 6α-methyl prednisolone given in the conventional anti-inflammatory dose range.

It is particularly convenient to formulate the steroid and the 1α-hydroxy vitamin D in combination, e.g. in dosage forms such as pills, capsules, ampoules for injection and the like containing the two components. The dose of 1α-hydroxy vitamin D in these formulations is preferably in the range set above for daily administration.

The ratio of the dosage of a corticoid administered daily or in each dosage unit to the dosage of 1α-hydroxy vitamin D is preferably in the range $5 \times 10^3$ to $2.5 \times 10^5$, more preferably $5 \times 10^3$ to $5 \times 10^4$, multiplied by a factor which is the required dose of prednisolone divided by the required dose of the corticoid (if other than prednisolone). Such required doses are readily known for the medical literature, for example Goodman and Gilman.

Osteoporosis is also associated with therapy involving some other drugs, notably diphenylhydantoin and related hydantoin antiepileptic drugs, barbiturates and immunosuppressive drugs. This condition can also be treated with 1α-hydroxy vitamin D and formulations can be prepared containing the vitamin, preferably in the above dose range, together with an effective dose of the drug.

Treatment of osteoporosis is often enhanced by administration of assimilable phosphorus, e.g. an alkali metal orthophsophate. Compositions containing 1α-hydroxy vitamin D together with a source of assimilable phosphate are thus also useful, with or without added corticoid.

Post menopausal osteoporosis

The daily dose and preferred unit dose of the vitamin should be in the range 0.02 to 5.0 µg, preferably 0.1 to 2.0 µg. This condition can be treated therapeutically or prophylactically by administration of 1α-hydroxy vitamin D$_3$. In many cases the treatment is more effective when combined with oestrogen replacement therapy that is estrogen treatment for 21 to 30 days followed by 5–7 days cessation to simulate the hormonal cycle. A progestagen may be used simultaneously.

Estrogens which may be used include synthetic drugs such as diethylstilbestrol and 17α-ethynyl oestradiol as well as natural estrogens such as esteone, estradiol, estriol and conjugated equine estrogens. Substances which are metabolised to estrogens (pro-estrogens) may also be used, for example those described in British Patent No. 1110792.

An estrogen will be used at its normal effective dose. In general, the ratio of the dose of the estrogen to the dose of vitamin will be in the range $2.5 \times 10^2$ to $1.25 \times 10^4$, preferably $5 \times 0^2$ to $2.5 \times 10^3$, multiplied by a factor which is the ratio of the estrogenic dose of diethyl stilboestrol divided by the estrogelic dose of the estrogen (where these is other than diethyl stilboestrol). Compositions may be formulated which contain the two drugs in the above dosage ranges.

The beneficial effect of combining estrogen replacement therapy with treatment with 1α-hydroxy vitamin D$_3$ is apparently due to the effect of the reduction by the estrogen (or proestrogen) of parathyroid hormone secretion, which together with the stimulus to bone formation provided by the 1α-hydroxy vitamin D$_3$, comprises an especially effective treatment (therapeutic or prophylactic) of oseteoporosis.

Care must naturally be exercised in the treatment of diseases other than most-menopausal osteoporosis to ensure that the estrogen or pro-estrogen does not produce unwanted hormonal effects.

Renal osteodystrophy

Individuals suffering from any degree of chronic renal disease can beneficially be treated with 1α-hydroxy vitamin D$_3$ in order to prevent induction of osteodystrophy, the dose range is preferably 0.02 to 5.0 µg, more preferably 0.1 to 2.0 µg per day.

Wounds and bone fractures

Healing of wounds and bone fractures may be promoted by administration of 1α-hydroxy vitamin D$_3$ in the range 0.02 µg to 5.0 µg, preferably 0.10 µg, to 2.0 µg.

Bone Pain

Bone pain due to bone tumours such as multiple myelomas may be alleviated by administration of 1α-hydroxy vitamin D$_3$ in the dose range 0.02 µg to 5.0 µg, preferably 0.10 µg to 2.0 µg.

We have further found that the above conditions, none of which are susceptible to treatment with vitamin D itself, can be treated by a 1α,25-dihydroxy vitamin D$_3$ in the same way and in the same dosage range as 1α-hydroxy vitamin D$_3$. Although 1α,25-dihydroxy vitamin D has previously been described as possessing enhanced vitamin D activity, it was not previously known that it could be used advantageously in the treatment of the above conditions with the exception of renal osteodystrophy which is a disease normally thought to be associated with an inability of the kidneys to produce 1α,25-dihydroxy vitamin D$_3$. As indicated above we have further found that 1α,25-dihydroxy-vitamin D$_3$, like 1α-hydroxy vitamin D$_3$, is rendered unstable by the presence of isomeric or other tenaceous impurities arising from its manufacture; it is consequently preferred to use in the above treatments and formulations 1α,25-dihydroxy vitamin D which has been purified to the substantial exclusive of isomeric or other impurities arising from manufacture preferably by crystallisation. The preparation of such material is described in our above application Ser. No. 362,339.

Veterinary applications of the new 1α-hydroxy-25-hydrogen vitamin D compounds and 1α-hydroxy-9,10-dihydrotachysterol include the prevention of hypocalcaemia in domestic animals, e.g. farmyard animals such as cattle and sheep, especially cows and ewes at or near parturition. 1α-Hydroxy vitamin D$_3$ is of particular value in this respect since the high activity and low toxicity of this compound enable it to be administered prophylactically at a low dosage over a period of time to, for example, a herd of animals, including animals having no previously history of hypocalcaemia. This is in contrast with the use of conventional vitamin D compounds in this field, since in view of the higher doses required when using compounds such as vitamin D$_3$ it is normal practice, inter alia on economic grounds and due to toxicity, to administer the vitamin only to animals having a previous history of hypocalcaemia.

It has also been found that the administration of effective doses of 1α-hydroxy-25-hydrogen vitamin D compounds, especially 1α-hydroxy vitamin D$_3$, to laying fowl has the effect of reducing the incidence of soft shelled eggs produced by the fowl, and such treatment comprises a further feature of the invention.

The invention also embraces poultry feed compositions containing 1α-hydroxy 25-hydrogen vitamin D compounds, especially 1α-hydroxy vitamin $D_3$, e.g. at a level of 0.2 to 0.2 μg, conveniently 1–8 μg of vitamin per kilogram of feed: feed concentrates are also provided containing the 1α-hydroxy vitamin $D_3$ compound at a concentration suitable to yield the above feed concentration on dilution with approximate feed components. Such a concentrate may contain other vitamins, nutrients, and/or beneficial minerals which will be at the same multiple of their effective concentration in the poultry feed as is the 1α-hydroxy vitamin D.

The invention is further illustrated by the following detailed. Examples. All temperatures are in degrees centigrade.

EXAMPLE 1

Orally administrable 1α-hydroxy vitamin $D_3$ compositions (a) 1α-hydroxy vitamin $D_3$ capsules 1α-hydroxy vitamin $D_3$ is dissolved in sterile arachis oil of low peroxide containing 0.1% w/w butylated hydroxyamisole as antioxidant to give a solution with a vitamin concentration of 40 μg/ml. ¼ ml portions of the resulting solution are encapsulated in gelatin by conventional techniques.

Dose—1–2 capsules per day.

Capsules were also prepared by the above method solutions containing 2.0 μg/ml and 4.0 μg/ml respectively of 1α-hydroxy vitamin $D_3$.

(b) Tri-vitamin preparation

Tablets comprising the following ingredients are prepared by conventional techniques:

| | |
|---|---|
| Vitamin A | 4000 u.s.p. units |
| Vitamin C | 75 mg |
| 1α-Hydroxy vitamin $D_3$ | 0.2–1 μg |

The preparation may optionally also contain 1 mg. of fluorine as a phsiologically compatible fluoride salt.

Dose—1 tablet per day.

(c) Deca-vitamin preparation (for adult use)

Tablets comprising the following ingredients are prepared by conventional techniques:

| | |
|---|---|
| Vitanin A | 25,000 u.s.p. units |
| Vitamin $B_1$ | 10 mg |
| Vitamin $B_2$ | 10 mg |
| Vitamin $B_6$ | 5 mg |
| Vitamin $B_{12}$ | 5 μg |
| Vitamin C | 200 mg |
| 1α-Hydroxy vitamin $D_3$ | 0.2–1 μg |
| Vitamin E | 15 I.U. |
| Calcium pantothenate | 20 mg |
| Nicotinamide | 100 mg |

The tablets may optionally also contain 1 mg of fluorine as a physiologically compatible fluoride salt and/or a mineral complex comprising the following elements in the form of physiologically compatible salts:

| | |
|---|---|
| Copper | 2 mg |
| Iodine | 0.15 mg |
| Iron | 12 mg |
| Magnesium | 65 mg |
| Manganese | 1 mg |
| Zinc | 1.5 mg |

Dose—1 tablet per day.

EXAMPLE 2

Deca-vitamin preparation (for infants and children)

Tablets comprising the following ingredients are prepared by conventional techniques:

| | |
|---|---|
| Vitamin A | 5000 u.s.p. units |
| Vitamin $B_1$ | 5 mg |
| Vitamin $B_2$ | 5 mg |
| Vitamin $B_6$ | 2 mg |
| Vitamin $B_{12}$ | 10 μg |
| Vitamin C | 100 mg |
| 1α-Hydroxy vitamin $D_3$ | 0.2–1 μg |
| Calcium pantothenate | 3 mg |
| Nicotinamide | 30 mg |

The tablets may optionally also contain a physiologically compatible fluoride salt or mineral complex in the quantities set out in (c) above.

Dose—1 tablet per day.

EXAMPLE 3

Feed composition for poultry

40 μg of 1α-hydroxy vitamin $D_3$ are dissolve in ethanol (100–500 ml) and the resulting solution is slurried with 2 kg of ground limestone. The ethanol is then removed under reduced pressure, with stirring of the slurry, and the resulting vitamin-containing solid is added to poultry feed at a rate of 20 g per kilogram of feed.

EXAMPLE 4

Capsules

| | |
|---|---|
| 20 μg | 1α-hydroxy vitamin $D_3$ |
| 100 ml | Arachis oil |
| 100 mg | butyrated hydroxytoluene |
| 5 g | prednisolone USP micronised |

The above components are mixed in a high speed homogeniser and filled into 1000 0.1 ml gelatine capsules each containing 0.02 μg vitamin and 5 mg steroid. 1 to 4 capsules to be given daily.

Similar capsules were prepared using 20 μg 1α,25-dihydroxy vitamin $D_3$.

EXAMPLE 5

Capsules

| 0.02 mg | 1α-hydroxy vitamin $D_3$ |
|---|---|
| 0.6 g | betamethasone |
| 0.1 g | butyrated hydroxyanisole |
| 100 ml | arachis oil |

The above components are mixed as in Example 4 and filled into 1000 0.1 ml gelatine capsules each containing 0.02 μg vitamin and 0.6 ml steroid. 1 to 4 capsules to be given daily.

Similar capsules were prepared using 0.02 mg 1α,25-dihydroxy vitamin $D_3$.

EXAMPLE 6

Capsules

| 5 mg | 1α-hydroxy vitamin $D_3$ |
|---|---|
| 5 g | prednisolone USP micronised |
| 100 ml | arachis oil |
| 100 mg | butyrated hydroxy toluene |

The above components are mixed in a high speed homogeniser and filled into 1000 0.1 ml gelatine capsules each containing 5.0 μg vitamin and 5 mg steroid. 1 to 4 capsules daily.

Similar capsules were prepared using 5 mg 1α,25-dihydroxy vitamin $D_3$.

EXAMPLE 7

Tablets 1 mg 1α-hydroxy vitamin $D_3$ are dissolved in 10 ml ethanol and 5 g lactose are added. Solvent is removed and the powder intimately mixed with

| 190 g | lactose |
|---|---|
| 1 g | stearic acid and |
| 4 g | triamcinnolone | and compressed into 1000 200 mg tablets, each containing 1 μg vitamin and 4 mg steroid. 1 to 2 tablets daily.

Similar tablets were prepared using 1 mg 1α,25-dihydroxy vitamin $D_3$.

EXAMPLE 8

Capsules

Capsules are prepared as in Example 5 each containing

| 0.5 μg | 1α-hydroxy vitamin $D_3$ |
|---|---|
| 0.7 mg | dexamethasone |
| 0.1 mg | butyrated hydroxy anisole |
| 0.1 ml | arachis oil |

Similar capsules were prepared containing 0.5 μg 1α,25-dihydroxy vitamin $D_3$.

EXAMPLE 9

Capsules

| 20 μg | 1α-hydroxy vitamin $D_3$ |
|---|---|
| 100 ml | arachis oil |
| 100 mg | butyrated hydroxytoluene |
| 20 mlg | 17α-ethynyloestradiol |

The above components are mixed in a high speed homogeniser and filled into 1000 0.1 ml gelatine capsules each containing 0.02 μg vitamin and 0.02 mg steroid. 1–3 capsules daily.

Similar capsules were prepared containing 20 μg 1α,25-dihydroxy vitamin $D_3$.

EXAMPLE 10

Capsules

Capsules were prepared as in Example 9 each containing:

| 0.25 μg | 1α-hydroxy vitamin $D_3$ |
|---|---|
| 0.25 mg | ethyl stilboestrol |
| 0.01 mg | butyrated hydroxy toluene |
| 0.1 ml | arachis oil |

1–4 capsules daily

Similar capsules were prepared containing 0.5 μg 1α-hydroxy vitamin $D_3$ or 0.25 μg 1α,25-dihydroxy vitamin $D_3$.

EXAMPLE 11

Tablets

| 0.67 mg | 1α-hydroxy vitamin $D_3$ and |
|---|---|
| 0.1 g | butyrated hydroxytoluene were dissolved in 5 ml ethanol and 5 g lactose added. Solvent was removed and the powder was mixed with |
| 192.75 g | lactose |
| 1.0 g | stearic acid |
| 1.25 g | conjugated equine oestrogens USP | and compressed into 1000 200 mg tablets. 1–3 tablets per day.

Similar tablets were prepared using 0.67 mg 1α,25-dihydroxy vitamin $D_3$.

We claim:

1. A method of treatment or prevention of vitamin D resistant diseases comprising administering to a human subject a pharmaceutical composition in unit dosage form containing from 0.2 to 5.0 μg of 1α-hydroxy vitamin $D_3$ and not exceeding 5.0 μg per day.

2. A method as claimed in claim 1, wherein the composition in unit dosage form is for oral administration.

3. A method as claimed in claim 1, wherein the pharmaceutical composition in unit dosage form contains from 0.2 to 1.0 μg of 1α-hydroxy vitamin $D_3$ and further contains additional active ingredients selected from the group consisting of essential trace elements, vitamins and mixtures thereof.

4. A method as claimed in claim 1, wherein the pharmaceutical composition also contains calcium and/or phosphorus in a physiologically available form.

5. A method as claimed in claim 1 in which the 1α-hydroxy vitamin $D_3$ is free of isomeric impurities.

6. A method as claimed in claim 5 wherein the 1α-hydroxy vitamin $D_3$ is in crystalline form.

7. A method as claimed in claim 1 wherein the disease is vitamin D resistant rickets, hypocalcaemia or bone disease.

8. A method as claimed in claim 7 wherein the hypocalcaemia or bone disease is due to biliary cirrhosis, steatorrhea, or malfunction of absorption.

9. A method as claimed in claim 7 wherein the hypocalcaemia or bone disease is due to hypoparathyroidism.

10. A method as claimed in claim 7 wherein the hypocalcaemia or bone disease is due to renal osteodystrophy.

11. A method as claimed in claim 7 wherein the hypocalcaemia or bone disease is due to osteoporosis.

12. A method as claimed in claim 7 wherein the hypocalcaemia or bone disease is due to treatment with dilantin, barbiturates and related anticonvulsant drugs.

13. A method as claimed in claim 11 wherein the osteoporosis is due to treatment with steroids.

* * * * *